United States Patent
Pervushin et al.

[11] Patent Number: 6,133,736
[45] Date of Patent: Oct. 17, 2000

[54] TRANSVERSE RELAXATION-OPTIMIZED SPECTROSCOPY (=TROSY)

[75] Inventors: Konstantin Pervushin, Zürich; Gerhard Wider, Herrliberg; Roland Riek, Rickenbach; Kurt Wüthrich, Wallisellen, all of Switzerland

[73] Assignee: Bruker AG, Fallanden, Switzerland

[21] Appl. No.: 09/164,278

[22] Filed: Oct. 1, 1998

[30] Foreign Application Priority Data

Oct. 18, 1997 [EP] European Pat. Off. ............. 97118127

[51] Int. Cl.[7] ...................................................... G01V 3/00
[52] U.S. Cl. ............................................ 324/307; 324/309
[58] Field of Search .................................. 324/307, 309, 324/318

[56] References Cited

PUBLICATIONS

G. Wagner: "Prospects for NMR of large proteing", Journal of Biomolecular NMR, vol. 3, 1993, pp. 375–385.

L.E. Kay et al.: "Pulse Sequences for Removal of the Effects of Cross Correlation between Dipolar and Chemical–Shift Anisotropy Relaxation Mechanisms ont eh Measurement of Heteronuclear T1 and T2 Values in Proteins", Journal of Magnetic Resonance, vol. 97, 1992, pp. 359–375.

J.Boyd et al: "Influence of cross–correlation between dipolar and chemical shift anisotropy relaxation mechanisms upon the transverse relaxation rates of 15–N in macromolecules", Chemical Physics Letters, vol. 187, No. 3, Dec. 6, 1991, pp. 317–324.

S. Wimperis et al.: "Relaxation–allowed cross–peaks in two–dimensional N.M.R. correlation spectroscopy", Molecular Physics, vol. 66, No. 5, 1989, pp. 897–919.

G. Bodenhausen et al.: "Natural Abundance Nitrogen–15 NMR by Enhanced Heteronuclear Spectroscpy", Chemical Physics Letters, vol. 69, No. 1, Jan. 1980, pp. 185–189.

N. Tjandra et al.: "Solution NMR Measurement of Amide Proton Chemical Shift Anisotropy in 15–N–Enriched Proteins. Correlation with Hydrogen Bond Length", vol. 119, Aug. 27, 1997, pp. 8076–8072.

*Primary Examiner*—Christine K. Oda
*Assistant Examiner*—Brij B. Shrivastav
*Attorney, Agent, or Firm*—Paul Vincent

[57] ABSTRACT

A method for obtaining a nuclear magnetic resonance (NMR) correlation spectrum of heteronuclear spin systems, in particular comprising large molecules, especially biological macromolecules in solution, the spin system being subjected to a homogeneous magnetic field $B_0$, being irradiated by a sequence of radio frequency (rf) pulses, is characterized in that the spin system comprises at least two kinds of spin ½ nuclei I and S being coupled to each other, whereby the sequence of rf pulses is chosen such that line broadening in the observed spectrum due to transverse relaxation ($T_2$) is significantly reduced because of cross correlation between dipole—dipole (DD) coupling of the spins and chemical shift anisotropy (CSA), giving rise to different relaxation rates of the individual multiplet components of the spin system and chosen such that the relaxation effects of the two different mechanisms cancel each other out to a large degree. Thus, even very large biological macromolecules can be measured.

19 Claims, 4 Drawing Sheets

TRANSVERSE RELAXATION-OPTIMIZED SPECTROSCOPY (=TROSY)

BACKGROUND OF THE INVENTION

Attenuated $T_2$ relaxation by mutual cancellation of dipole—dipole coupling and chemical shift anisotropy indicates an avenue to NMR structures of very large biological macromolecules in solution. In this patent specification, the numbers in parenthesis refer to the references listed following the description of the preferred embodiment. The following definitions are used throughout this specification for reasons of conciseness:

Abbreviations: NMR, nuclear magnetic resonance; rf, radio-frequency; 2D, two-dimensional; FID, free induction decay; DD, dipole—dipole; CSA, chemical shift anisotropy; COSY, correlation spectroscopy; TROSY, transverse relaxation-optimized spectroscopy; PFG, pulsed field gradient; ftz homeodomain; fushi tarazu homeodomain polypeptide of 70 amino acid residues, with the homeodomain in positions 3–62.

Fast transverse relaxation of $^1H$, $^{15}N$ and $^{13}C$ by dipole—dipole coupling (DD) and chemical shift anisotropy (CSA) modulated by rotational molecular motions has a dominant impact on the size limit for biomacromolecular structures that can be studied by NMR spectroscopy in solution. TROSY (Transverse Relaxation-Optimized SpectroscopY) is a new approach for suppression of transverse relaxation in multidimensional NMR experiments, which is based on constructive use of interference between DD coupling and CSA. For example. a TROSY-type two-dimensional $^1H$, $^{15}N$-correlation experiment with a uniformly $^{15}N$-labeled protein in a DNA complex of molecular weight 17 kDa at a $^1H$ frequency of 750 MHz showed that $^{15}N$ relaxation during $^{15}N$ chemical shift evolution and $^1H^N$ relaxation during signal acquisition are both significantly reduced by mutual compensation of the DD and CSA interactions. The reduction of the linewidths when compared with a conventional two-dimensional $^1H$, $^{15}N$-correlation experiment was 60% and 40%, respectively, and the residual linewidths were 5 Hz for $^{15}N$ and 15 Hz for $^1H^N$ at 4° C. Since the ratio of the DD and CSA relaxation rates is nearly independent of the molecular size, a similar percentagewise reduction of the overall transverse relaxation rates is expected for larger proteins. For a $^{15}N$-labeled protein of 150 kDa at 750 MHz and 20° C. one predicts residual linewidths of 10 Hz for $^{15}N$ and 45 Hz for $^1H^N$, and for the corresponding uniformly $^{15}N$, $^2H$-labeled protein the residual linewidths are predicted to be smaller than 5 Hz and 15 Hz, respectively. The TROSY principle should benefit a variety of multidimensional solution NMR experiments, especially with future use of yet somewhat higher polarizing magnetic fields than are presently available, and thus largely eliminate one of the key factors that limit work with larger molecules.

Nuclear magnetic resonance (NMR) spectroscopy with proteins based on observation of a small number of spins with outstanding spectral properties, which may either be present naturally or introduced by techniques such as site-specific isotope labeling, yielded biologically relevant information on human hemoglobin (M=65000) as early as 1969 (Shulman, R. G., Ogawa, S., Wüthrich, K., Yamane, T., Peisach, J. & Blumberg, W. E. (1996) *Science* 165, 251–257), and subsequently also for significantly larger systems such as, for example, immunoglobulins (Arata, Y., Kato, K., Takahashi, H. & Shimada, I. (1994) Methods in Enzymology 239 440–464). In contrast, the use of NMR for de novo structure determination (Wüthrich, K. (1996) *NMR of Proteins and Nucleic Acids* (Wiley, New York); Wüthrich, K. (1995) *NMR in Structure Biology* (World Scientific, Singapore)) has so far been limited to relatively small molecular sizes, with the largest NMR structure below molecular weight 30000. Although NMR in structural biology may, for practical reasons of coordinated use with X-ray crystallography (Wüthrich, K. (1995) *Acta Cryst.* D 51, 249–270), focus on smaller molecular sizes also in the future, considerable effort goes into attempts to extend the size limit to bigger molecules (for example, Shan, X., Gardner, K. H., Munhandiram, D. R., Rao, N. S., Arrowsmith, C. H. & Kay, L. E. (1996) *J. Am. Chem. Soc.* 118, 6570–6579; Wagner, G. (1993) *J. Biomol, NMR* 3, 375–385; Nietlispach, D., Clowes, R. T., Broadhurst, R. W., Ito, Y., Keeler, J., Kelly, M., Ashurst, J., Oschkinat, H., Domaille, P. J. & Laue, E. D. (1996) *J. Am. Chem. Soc.* 118, 407–415). Here we introduce "transverse relaxation-optimized spectroscopy" (TROSY) and present experimental data and theoretical considerations showing that this novel approach is capable of significantly reducing transverse relaxation rates and thus overcomes a key obstacle opposing solution NMR of larger molecules (Wagner, G. (1993) *J. Biomol. NMR* 3, 375–385).

At the high magnetic fields typically used for studies of proteins and nucleic acids, chemical shift anisotropy interaction (CSA) of $^1H$, $^{15}N$ and $^{13}C$ nuclei forms a significant source of relaxation in proteins and nucleic acids, in addition to dipole—dipole (DD) relaxation. This leads to increase of the overall transverse relaxation rates with increasing polarizing magnetic field, $B_0$. Nonetheless, transverse relaxation of amide protons in larger proteins at high fields has been successfully reduced by complete or partial replacement of the non-labile hydrogen atoms with deuterons and, for example, more than 90% of the $^{15}N$, $^{13}C^\alpha$ and $^1H^N$ chemical shifts were thus assigned in the polypeptide chains of a protein-DNA complex of size 64000 (Shan, X., Gardner, K. H., Munhandiram, D. R., Rao, N. S., Arrowsmith, C. H. & Kay, L. E. (1996) *J. Am. Chem. Soc.* 118, 6570–6579). TROSY uses spectroscopic means to further reduce $T_2$ relaxation based on the fact that cross-correlated relaxation caused by DD and CSA interference gives rise to different relaxation rates of the individual multiplet components in a system of two coupled spins ½, I and S, such as, for example, the $^{15}N$—$^1H$ fragment of a peptide bond (Guéron, M., Leroy, J. L. & Griffey, R. H. (1983) *J. Am. Chem. Soc.* 105, 7262–7266; Tjandra, N., Szabo, A. & Bax, A. (1996) *J. Am. Chem. Soc.* 118, 6986–6991). Theory shows that at $^1H$ frequencies near 1 GHz nearly complete cancellation of all transverse relaxation effects within a $^{15}N$—$^1H$ moiety can be achieved for one of the four multiplet components. TROSY observes exclusively this narrow component, for which the residual linewidth is then almost entirely due to DD interactions with remote hydrogen atoms in the protein. These can be efficiently suppressed by $^2H$-labeling, so that in TROSY-type experiments the accessible molecular size for solution NMR studies is no longer primarily limited by $T_2$ relaxation.

SUMMARY OF THE INVENTION

We consider a system of two scalar coupled spins ½, I and S, with a scalar coupling constant $J_{IS}$, which is located in a protein molecule. $T_2$ relaxation of this spin system is dominated by the DD coupling of I and S and by CSA of each individual spin, since the stereochemistry of the polypeptide chain restricts additional interactions of I and S to weak scalar and DD couplings with a small number of remote protons, $I_k$. The relaxation rates of the individual multiplet components of spin S in a single quantum spectrum may then be widely different (Guéron, M., Leroy, J. L. & Griffey, R. H. (1983) *J. Am. Chem. Soc.* 105, 7262–7266; Farrar, T. C. & Stringfellow, T. C. (1996) in *Encyclopedia of MMR* eds. Grant, D. M. & Harris, R. K. (Wiley, New York), Vol. 6, pp. 4101–4107; Vold, R. R. & Vold R. L. (1978) *Prog. NMR Spectrosc.* 12, 79–133). They can be described using the single-transition basis operators $$S_{12}^{\pm}$$

and $$S_{34}^{\pm}$$

(Ernst R. R., Bodenhausen, G. & Wokaun, A. (1987) *The Principles of Nuclear Magnetic Resonance in One and Two Dimensions* (Clarendon Press, Oxford)), which refer to the transitions 1→2 and 3→4 in the standard energy-level diagram for a system of two spins ½, and are associated with the corresponding resonance frequencies, $$\omega_S^{12} = \omega_S + \pi J_{IS} \text{ and } \omega_S^{34} = \omega_S - \pi J_{IS}$$

(Ernst, R. R., Bodenhauren, G. & Wokaun, A. (1987) *The Principles of Nuclear Magnetic Resonance in One and Two Dimensions* (Clarendon Press, Oxford); Abragam, A. (1961) *The Principles of Nuclear Magnetism* (Clarendon Press, Oxford); Goldman, M. (1984) *J. Magn. Reson.* 60, 437–452; London, R. E. (1990) *J. Magn. Reson.* 86, 410–415):

$$\frac{d}{dt}\begin{bmatrix}\langle S_{12}^{\pm}\rangle \\ \langle S_{34}^{\pm}\rangle\end{bmatrix} = -\begin{bmatrix} \pm i\omega_S^{12} + R_{1212} + \frac{1}{T_{2S}} + \frac{1}{2T_{1I}} & 3(p^2 - \delta_I^2)J(\omega_I) - \frac{1}{2T_{1I}} \\ 3(p^2 - \delta_I^2)J(\omega_I) - \frac{1}{2T_{1I}} & \pm i\omega_S^{34} + R_{3434} + \frac{1}{T_{2S}} + \frac{1}{2T_{1I}} \end{bmatrix} \cdot \begin{bmatrix}\langle S_{12}^{\pm}\rangle \\ \langle S_{34}^{\pm}\rangle\end{bmatrix} \quad [1]$$

$\omega_S$ and $\omega_I$ are the Larmor frequencies of the spins S and I, $T_{2S}$ and $T_{1I}$ account for the transverse relaxation of spin S and the longitudinal relaxation time of spin I, respectively, by all mechanisms of relaxation except DD coupling between the spins S and I and CSA of the spins S and $$I.p = \frac{1}{2\sqrt{2}}\gamma_I \gamma_S h/r_{IS}^3,$$

$$\delta_S = \frac{1}{3\sqrt{2}}\gamma_S B_0 \Delta\sigma_S$$

$$\text{and } \delta_I = \frac{1}{3\sqrt{2}}\gamma_I B_0 \Delta\sigma_I,$$

where $\gamma_I$ and $\gamma_S$ are the gyromagnetic ratios of I and S, h is the Planck constant divide by $2\pi$, $r_{IS}$ the distance between S and I, $B_0$ the polarizing magnetic field, and $\Delta\sigma_S$ and $\Delta\sigma_I$ are the differences between the axial and the perpendicular principal components of the axially symmetric chemical shift tensors of spins S and I, respectively. $R_{1212}$ and $R_{3434}$ are the transverse relaxation rates of the individual components of the S doublet (Farrar, T. C. & Stringfellow, T. C. (1996) in *Encyclopedia of NMR* eds. Grant, D. M. & Harris, R. K. (Wiley, New York), Vol. 6, pp. 4101–4107 given by Eqs. [2] and [3], $$R_{1212} = (p-\delta_S)^2(4J(0)+3J(\omega_S))+p^2(J(\omega_I-\omega_S)+3J(\omega_I)+6J(\omega_I+\omega_S))+3\delta_I^2 J(\omega_I) \quad [2]$$

$$R_{3434} = (p+\delta_S)^2(4J(0)+3J(\omega_S))+p^2(J(\omega_I-\omega_S)+3J(\omega_I)+6J(\omega_I+\omega_S))+3\delta_I^2 J(\omega_I) \quad [3]$$

where $J(\omega)$ represents the spectral density functions at the frequencies indicated:

$$J(\omega) = \frac{2\tau_c}{5(1+(\tau_c\omega)^2)} \quad [4]$$

In deriving the Eqs. [2] and [3], parallel orientation of the principal symmetry axis of the chemical shift tensor and the vector $r_{IS}$ was assumed. These equations show that whenever CSA and DD coupling are comparable, i.e., $p \approx \delta_S$, the resonance at frequency $$\omega_S^{12}$$

may exhibit slow transverse relaxation even for very large molecules.

For a treatment of the relaxation of spin I by Eq. [1] the symbols I and S can simply be interchanged. The single-transition operators $$I_{12}^{\pm} \text{ and } I_{24}^{\pm}$$

then refer to the transitions between the energy levels 1→3 and 2→4, respectively, which are associated with the frequencies $$\omega_I^{13} = \omega_I + \pi J_{IS} \text{ and } \omega_I^{24} = \omega_I - \pi J_{IS},$$

and the relaxation rates $R_{1313}$ and $R_{2424}$ are determined by equations obtained by permutation of the S and I indices in Eqs. [2] and [3], respectively.

To evaluate the contributions from other mechanisms of relaxation we identify I and S as the $^1H^N$ and $^{15}N$ spins in a $^{15}N$–$^1H$ moiety. The relaxation of $^{15}N$ is then mainly determined by the CSA of $^{15}N$ and the DD interactions with the directly attached proton (Peng, J. W. & Wagner, G. (1992) *J. Magn. Reson.* 98, 308–332), so that the contributions from other interactions, $1/T_{1S}$ and $1/T_{2S}$, can to a good approximation be neglected. For $^1H^N$, $1/T_{1I}$ and $1/T_{2I}$ are dominated by DD interactions with other protons $I_k$ at distance $r_k$. These can be accounted for by spectral density functions $J_k(\omega)$, which describe the motions of the vectors joining the individual $^1H^N$–$^1H_k$ spin pairs (Peng, J. W. & Wagner, G. (1992) *J. Magn. Reson.* 98, 308–332):

$$1/T_{1I} = \sum_k (\gamma_I^2 h/2r_k^3)^2(J_k(0) + 3J_k(\omega_I) + 6J_k(2\omega_I)), \quad [5]$$

-continued $$1/T_{2I} = \sum_k (\gamma_I^2 \hbar/2r_k^3)^2 \left(\frac{5}{2}J_k(0) + \frac{9}{2}J_k(\omega_I) + 3J_k(2\omega_I)\right). \quad [6]$$

Here, the equations [1] to [6] were used to calculate theoretical lineshapes of spin multiplets for given sets of the relaxation parameters, which were subsequently compared with the experimental NMR data. In particular, the in-phase absorptive spectrum was calculated using Eq. [7] (Abragam, A. (1961) *The Principles of Nuclear Magnetism* (Clarendon Press, Oxford)), $$I(\omega)=Re[V A^{-1}V], \quad [7]$$

where V=(1,1) and the relaxation matrix A is the (2×2) matrix on the right hand side of Eq. [1].

In an embodiment of the invention a WATERGATE pulse sequence is used to suppress NMR signals from water.

DESCRIPTION OF THE PREFERRED EMBODIMENT

NMR spectra were recorded on Bruker DRX 750 and Varian Unityplus 400 spectrometers with a 2 mM solution of the specific 1:1 complex formed between a uniformly $^{15}$N-labeled 70-residue fushi tarazu (ftz) homeodomain polypeptide and an unlabeled 14-base pair DNA duplex (Percival-Smith, A., Müller, M., Affolter, M. & Gehring, W. J. (1990) *EMBO J.* 9, 3967–3974; Qian, J. Q., Furukubo-Tokunaga, K., Resendez-Perez, D. Müller, M., Gehring, W. J. & W üthrich, K. (1994) *J. Mol. Biol.* 238, 333–345) in 95% $^1$H$_2$O/5% $^2$H$_2$O at pH 6.0 and 4° C.

The isotropic rotational correlation time, $\tau_c$, of the complex was estimated from the $T_1/T_2$ ratio of the relaxation times of the backbone $^{15}$N nuclei (Kay, L. E., Torchia, D. A. & Bax, A. (1989) *Biochemistry* 28, 8972–8979). The experimental schemes of Farrow et al. (Farrow, N. A., Muhandiram, R., Singer, A. U., Pascal, S. M., Kay, C. M., Gish, G., Shoelson, S. E., Pawson T., Forman-Kay, J. D., Kay, L. E. (1994) *Biochemistry* 33, 5984–6003) were used for measurements of $T_1(^{15}N)$ and $T_2(^{15}N)$ for backbone nitrogen atoms.

The TROSY (Transverse Relaxation-Optimized SpectroscopY) approach (FIG. 1) and conventional [$^{15}$N, $^1$H]-COSY (Müller, L. (1979) *J. Am. Chem. Soc.* 101, 4481–4484; Bodenhausen, G. & Ruben, D. J. (1980) *Chem. Phys. Lett.* 69, 185–189) experiments were used to correlate $^1$H and $^{15}$N resonances. For all spectra $t_{1\,max}$=90 ms and $t_{2\,max}$=171 ms were used. In TROSY the evolution of the I,S spin system due to the $^1J_{IS}$ scalar coupling was not refocused during $t_1$ and $t_2$, thus avoiding suppression of cross-correlated relaxation during these periods. To obtain the pure absorptive spectrum containing only the most slowly relaxing component of the 2D multiplets, the scheme of FIG. 1 was employed.

The NMR experiments with the uniformly $^{15}$N-labeled ftz homeodomain complexed with a 14-base pair DNA duplex were performed at 4° C. The $T_1/T_2$ ratio of $^{15}$N was used to estimate the effective global correlation time, $\tau_c$, of the complex (Kay, L. E., Torchia, D. A. & Bax, A. (1989) *Biochemistry* 28, 8972–8979). For the backbone amide groups, average $T_1(^{15}N)$ and $T_2(^{15}N)$ values of 0.720±0.03 and 0.042±0.005 s, respectively, were measured at 400 MHz, resulting in a global rotational correlation time of $\tau_c$=20±2 ns. This $\tau_c$ value corresponds to that expected for a spherical protein of size 40 kDa in $H_2O$ solution at 35° C.

Figure 2:
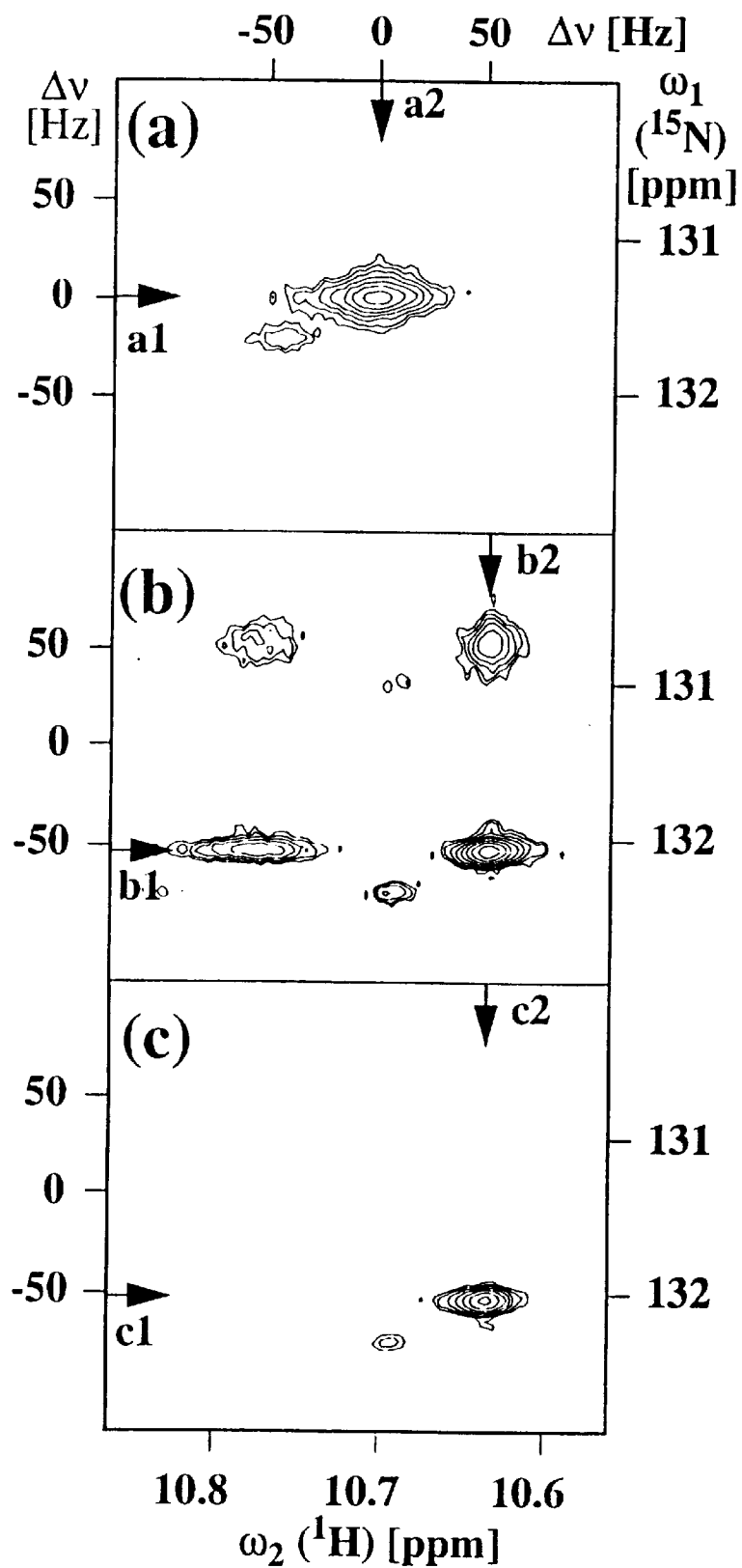
FIG. 2. Contour plots of $^{15}$N, $^1$H correlation spectra showing the indole $^{15}$N–$^1$H spin system of Trp 48 recorded in a 2 mM solution of uniformly $^{15}$N-labeled ftz homeodomain complexed with an unlabeled 14-bp DNA duplex in 95% H$_2$O/5% $^2$H$_2$O at 4° C., pH=6.0, measured at $^1$H frequency of 750 MHz. (a) Conventional broad-band decoupled [$^{15}$N, $^1$H]-COSY spectrum (Müller, L. (1979) *J. Am. Chem. Soc.* 101, 4481–4484. Bodenhausen, G. & Ruben, D. J. (1980) *Chem. Phys. Lett.* 69, 185–189). The evolution due to the $^1$J($^1$H, $^{15}$N) scalar coupling was refocused in the $\omega_1$ and $\omega_2$ dimensions by a 180° proton pulse in the middle of the $^{15}$N evolution time $t_1$, and by WALTZ composite pulse decoupling of $^{15}$N during data acquisition, respectively; (b) conventional [$^{15}$N, $^1$H]-COSY spectrum recorded without decoupling during $t_1$ and $t_2$; (c) TROSY-type $^{15}$N, $^1$H correlation spectrum recorded with the pulse scheme of FIG. 1. Chemical shifts relative to DSS in ppm and shifts in Hz relative to the center of the multiplet are indicated in both dimensions. The arrows identify the locations of the cross sections shown in FIG. 3.
Figure 3:
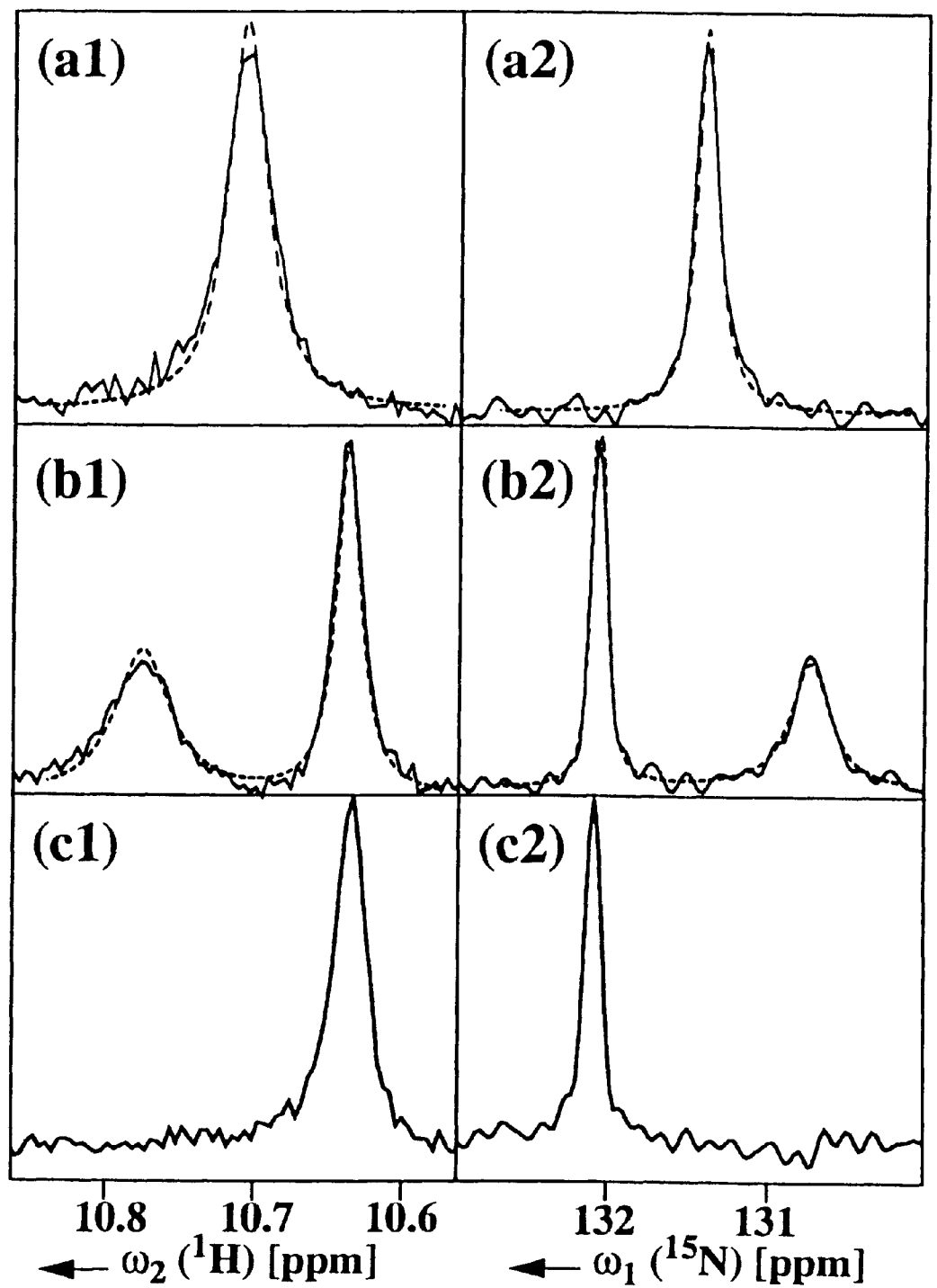
FIG. 3. Cross sections through the spectra of FIG. 2 (solid lines). To facilitate a comparison of the linewidths in the different spectra the cross sections were normalized to the same maximal signal amplitude. (a1), (a2), . . . refer to the arrows in FIG. 2. Simulated line shapes (dashed lines in (a) and (b)) were calculated using $^1$J($^1$H, $^{15}$N)=–105 Hz, a rotational correlation time of $\tau_c$=20 ns, and chemical shift anisotropies of $\Delta\sigma_H$=–16 ppm and $\Delta\sigma_N$=–160 ppm. A long-range scalar coupling $^2$J($^1$H$^{\delta 1}$, $^{15}$N$^{\epsilon 1}$)=–5 Hz was included in the simulation of the $^{15}$N lineshapes (Bystrov, V. F. (1976) *Prog. NMR Spectrosc.* 10, 41–81), but possible effects of the small scalar couplings $^3$J($^1$H$^{\delta 1}$, $^1$H$^{\epsilon 1}$) and $^3$J($^1$H$^{\zeta 2}$, $^{15}$N$^{\epsilon 1}$) were neglected. For $^1$H$^N$ the relaxation due to DD coupling with other protons in the non-deuterated complex was approximated by 3 protons placed at a distance of 0.24 nm from $^1$H$^N$.

The FIG. 2 shows a small region from $^{15}N$–$^1H$ correlation spectra of the ftz homeodomain-DNA complex that contains the resonance of the indole $^{15}N$–$^1H$ moiety of Trp48, which is buried in the core of the protein (Qian, J. Q., Furukubo-Tokunaga, K., Resendez-Perez, D. Müller, M., Gehring, W. J. & Wüthrich, K. (1994) *J. Mol. Biol.* 238, 333–345). In the conventional [$^{15}N$, $^1H$]-COSY experiment (Müller, L. (1979) *J. Am. Chem. Soc.* 101, 4481–4484; Bodenhausen, G. & Ruben, D. J. (1980) *Chem. Phys. Lett.* 69, 185–189), decoupling of $^1H$ and $^{15}N$ during the time periods $t_1$ and $t_2$, respectively, leads to detection of a single correlation peak per $^{15}N$–$^1H$ moiety (FIG. 2a). If the same [$^{15}N$, $^1H$]-COSY spectrum is recorded without decoupling, four cross peaks are observed per $^{15}N$–$^1H$ moiety, which show largely different linewidths (FIG. 2b). The cross peak at ($\omega_1$=130.7 ppm, $\omega_2$=10.78 ppm) exhibits the broadest linewidths in both dimensions, which shows that it originates from the rapidly relaxing components of both $^1H^N$ and $^{15}N$. One-dimensional cross sections taken along $\omega_2$ and $\omega_1$ at the positions indicated by arrows in the spectra presented in FIG. 2 show that the two cross peaks at ($\omega_1$=132.1 ppm, $\omega_2$=10.78 ppm) and ($\omega_1$=130.7 ppm, $\omega_2$=10.65 ppm) are broadened either along $\omega_1$ or along $\omega_2$ (FIG. 3). The cross peak at ($\omega_1$=132.1 ppm, $\omega_2$=10.65 ppm) displays narrow linewidths in both dimensions, showing that it originates from the two slowly relaxing components of the $^{15}N$–$^1H$ doublets. The TROSY-type correlation experiment, which does not use decoupling either during $t_1$ or $t_2$, contains only this narrowest correlation peak (FIG. 2c), which shows about 60% and 40% decrease in the linewidths of the $^{15}N$ and $^1H$ resonances, respectively, when compared to the collapsed cross peak in the conventional, broadband-decoupled spectrum (FIG. 2).

The fits of the experimental line shapes shown in FIG. 3 were obtained with line shape calculations using the parameters $\tau_c$=20 ns and $^1J(^1H, ^{15}N)$=105 Hz, where the chemical shift anisotropies, $\Delta\sigma_H$ and $\Delta\sigma_N$, were adjusted for the best fit. Since there was an otherwise unaccountable deviation from the Lorentzian lineshape we included a long-range scalar coupling $^2J(^1H^{\delta 1}, ^{15}N^{\epsilon 1})$=–5 Hz (24) in the calculations, and $T_1$ and $T_2$ relaxation of $^1H^N$ due to dipole—dipole coupling with other protons was modeled by placing 3 protons at a distance of 0.24 nm from $^1H^N$. Application of one or a series of 180° pulses on spin I during the evolution of spin S interchanges the slowly and rapidly relaxing components of the S multiplet, which results in averaging of the slow and fast relaxation rates and elimination of the CSA/DD interference (Palmer, A. G., Skelton N. J., Chazin, W. J., Wright, P. E. & Rance, M. (1992) *Mol. Phys.* 75, 699–711; Kay, L. E., Nicholson, L. K., Delaglio, F., Bax, A. & Torchia, D. A. (1992) *J. Magn. Reson.* 97, 359–375). Indeed, the line shapes of the $^1H^N$ and $^{15}N$ resonances measured with conventional [$^{15}N$, $^1H$]-COSY are well reproduced if the average of the two relaxation rates is used in the simulation (FIG. 3, a1 and b1). The best fit values of $\Delta\sigma_H$=–16 ppm and $\Delta\sigma_N$=–160 ppm correspond closely to the experimentally measured chemical shift anisotropies of $^1H$ and $^{15}N$ in $^{15}N$–$^1H$ moieties: with solid state NMR studies of $^{15}N$–$^2D$ moieties, values for $\Delta\sigma_D$ near –14 ppm (Michal, C. A., Wehman, J. C., Jelinski, L. W. (1996) *J. Magn. Reson. Ser. B.* 111, 31—39 and "28" with—Hiyama, Y., Niu, C., Silverton, J. V., Bavoso, A. & Torchia, D. A. (1988) *J. Am. Chem. Soc.* 110, 2378–2383) and for $\Delta\sigma_N$ of –160 ppm (28) were determined; independently, solution NMR experiments yielded values for $\Delta\sigma_H$ of backbone amide protons in the range –8 to –17 ppm (A. Bax, personal communication) and $\Delta\sigma_N$ near –170 ppm (Tjandra, N., Szabo, A. & Bax, A. (1996) *J. Am. Chem. Soc.* 118, 6986–6991).

In the experiments with the ftz homeodomain-DNA complex described in this paper the overall transverse relaxation rates of $^{15}N$ and $^1H^N$ in the indole $^{15}N$–$^1H$ moiety of a buried tryptophan were reduced by 60% and 40%, respectively, when using a TROSY-type [$^{15}N$, $^1H$]-correlation experiment instead of the conventional [$^{15}N$, $^1H$]-COSY scheme. At a first glance this may appear to be a modest improvement, but a closer look reveals that DD coupling with remote protons, which could be nearly completely suppressed by replacement of the non-labile hydrogen atoms with $^2H$ (e.g., Shan, X., Gardner, K. H., Munhandiram, D. R., Rao, N. S., Arrowsmith, C. H. & Kay, L. E. (1996) *J. Am. Chem. Soc.* 118, 6570–6579; Nietlispach, D., Clowes, R. T., Broadhurst, R. W., Ito, Y., Keeler, J., Kelly, M., Ashurst, J., Oschkinat, H., Domaille, P. J. & Laue, E. D. (1996) *J. Am. Chem. Soc.* 118, 407–415), accounts for 95% of the residual $T_2(^1H^N)$ relaxation and 75% of the residual $T_2(^{15}N)$ relaxation. In a corresponding DNA complex with the perdeuterated ftz homeodomain the reduction of the $T_2$ relaxation rates of the $^{15}N$–$^1H$ moieties by the use of TROSY at 750MHz would be about 40-fold for $^1H^N$ and about 10-fold for $^{15}N$.

Using the equations [1]–[6] with $\Delta\sigma_H$=–16 ppm, $\Delta\sigma_N$=–160 ppm, $r_{HN}$=0.101 nm and parallel orientation of the principal axis of the CSA tensor with the vector $r_{HN}$ we evaluated the dependence of the residual $T_2$ relaxation rates of $^{15}N$ and $^1H$ in TROSY-type experiments on the polarizing magnetic field $B_0$ and the molecular size. These calculations showed that nearly complete compensation of $T_2$ relaxation due to DD and CSA within the $^{15}N$–$^1H$ moieties is obtained at a $B_0$ strength corresponding to a $^1H$ frequency near 1100 MHz, i.e., at this field strength $(p-\delta_S)\cong 0$ and $(p-\delta_I)\cong 0$ in Eq. [2]. Theory further predicts that the residual TROSY $T_2$ relaxation rates due to DD and CSA interactions within the $^{15}N$–$^1H$ fragment are practically independent of the molecular size. For perdeuterated proteins the size limit for TROSY-type [$^{15}N$, $^1H$]-correlation experiments is thus not critically determined by $T_2$ relaxation, but one needs nonetheless to consider that the effect of deuteration of the nonlabile proton sites in the protein is dependent on conformation. For the $^{15}N$–$^1H$ moieties in β-sheet secondary structure, DD and CSA interactions within the $^{15}N$–$^1H^N$ fragment are the only sources of transverse relaxation that need to be considered, whereas in α-helices the two sequentially adjacent $^1H^N$ protons (Wüthrich, K. (1986) *NMR of Proteins and Nucleic Acids* (Wiley, New York)) contribute significantly to the transverse relaxation of the $^{15}N$ and $^1H^N$ spins.

Figure 4:
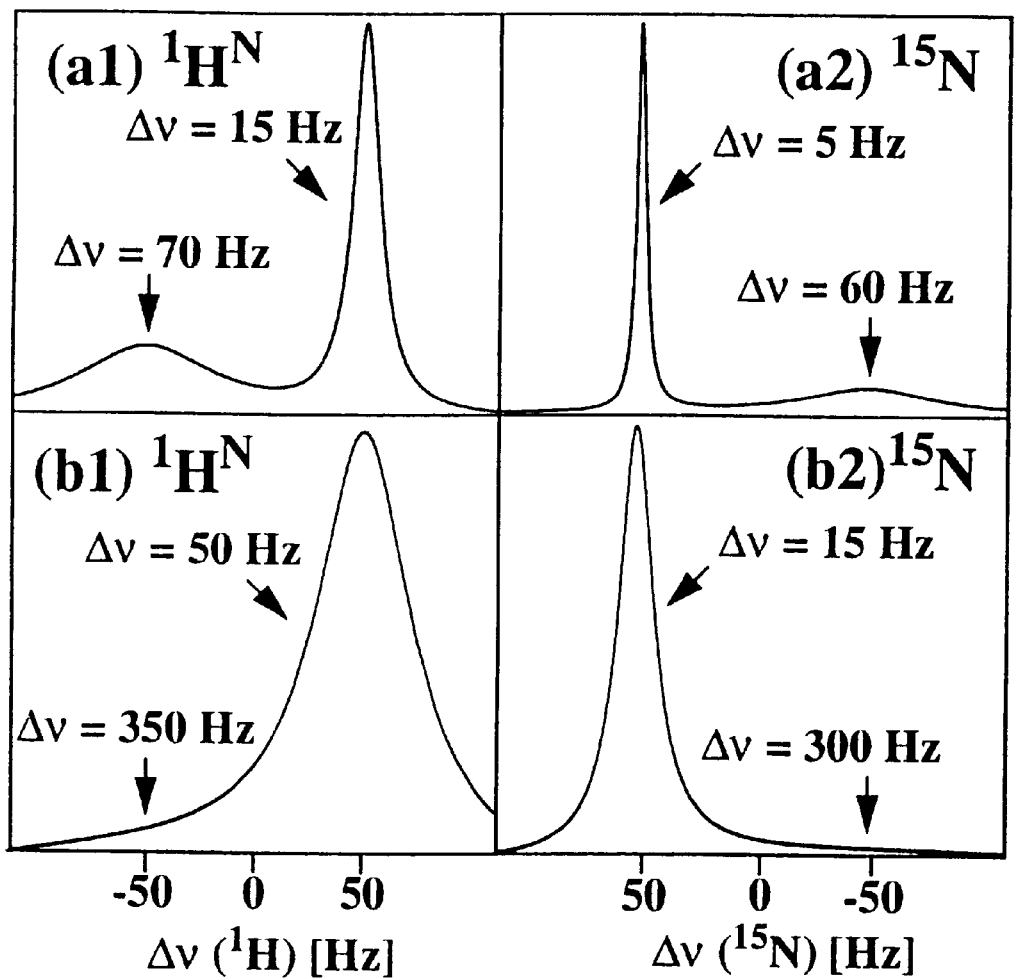
FIG. 4. $^1$H and $^{15}$N lineshapes predicted for the broad and narrow multiplet components of $^1$H$^N$ and $^{15}$N of the $^{15}$N–$^1$H moiety in a [$^{15}$N, $^1$H]-COSY experiment of the type of FIG. 3 b1 and b2 for large proteins in H$_2$O solution at 20° C. and a $^1$H frequency of 750 MHz. (a1) and (a2): Spherical protein of size 150 kDa. For the calculation a rotational correlation time of 60 ns, $\Delta\sigma_H$=–16 ppm and $\Delta\sigma_N$=–160 ppm were used, and all nonlabile protons were replaced with deuterons. Relaxation due to DD coupling with other labile protons was modelled by placing two protons at a distance of 0.29 nm from $^1$H$^N$. The full linewidths at half height are indicated. (b1) and (b2): Spherical protein of size 800 kDa. The calculation used $\tau_c$=320 ns and otherwise the same parameters as in (a).

In order to provide a tangible illustration (FIG. 4) we calculated the $^1H^N$ and $^{15}N$ line shapes for two perdeuterated spherical proteins in $^1H_2O$ solution with rotational correlation times $\tau_c$ of 60 and 320 ns, which corresponds to molecular weights of 150 kDa and 800 kDa, respectively. A magnetic field $B_0$ corresponding to a resonance frequency 750 MHz for protons was assumed. To account for the worst possible situation for DD interaction with remote protons, two protons were placed at 0.29 nm from $^1H^N$. The linewidth of the narrow component of the $^{15}N$ doublet increases only slightly with molecular weight and is about 5 Hz at 150 kDa and 15 Hz for a 800 kDa protein (FIG. 4). The $^1H^N$ linewidth depends more strongly on the residual DD interactions with remote protons and is about 15 Hz at 150 kDa and 50 Hz for a 800 kDa protein. For the 150 kDa protein these numbers correspond to 10-fold and 4-fold reduction of the $^{15}$N and $^1$H$^N$ TROSY linewidths, respectively, when compared with a conventional [$^{15}$N, $^1$H]-COSY experiment with broadband decoupling of $^{15}$N and $^1$H. For large molecular sizes the experimental scheme of FIG. 1 may in principle be further improved by elimination of the 180° refocusing rf-pulses during the INEPT transfers, since during the INEPT mixing times these pulses mix the multiplet components with slow and fast T$_2$ relaxation in a similar way as during the entire experiment in conventional [$^{15}$N, $^1$H]-COSY. The elimination of decoupling sequences and 180° pulses from TROSY-type NMR pulse sequences may also have implications for future probe designs, since the constraints by the requirements for minimal radio frequency heating and maximal B$_1$ homogeneity may then be relaxed, permitting a better optimization of other paramters such as sensitivity or sample diameter.

The TROSY principle drastically reduces all major sources of relaxation thoughout the entire NMR experiment, including signal acquisition, and is clearly distinct from the use of heteronuclear multiple-quantum coherence to reduce dipolar relaxation between heteronuclei (Griffey, R. H. & Redfield, A. G. (1987) *Quart. Rev. Biophys.* 19, 51–82), which was previously used for measurements of $^3J_{H\alpha H\beta}$ scalar coupling constants in proteins (Grzesiek, S., Kuboniwa, H., Hinck, A. P. & Bax, A. (1995) *J. Am. Chem. Soc.* 117, 5312–5315). Heteronuclear multiple-quantum coherences are subject to dipolar relaxation with remote spins as well as to CSA relaxation, which limits the use of these coherences at high polarizing magnetic fields. Moreover, the slow relaxation of the multiple-quantum coherences cannot be used during signal acquisition (Abragam, A. (1961) *The Principles of Nuclear Magnetism* (Clarendon Press, Oxford)), which is critical for large molecules.

The following are some initial considerations on practical applications of the TROSY principle. (i) Since only one of the four multiplet components of $^{15}$N–$^1$H moiety is retained in TROSY-type experiments, the conventional [$^{15}$N–$^1$H]-COSY is intrinsically more sensitive. However, for measurements with proteins at $^1$H frequencies higher than 500 MHz, TROSY will provide a much better ratio of signal height to noise. (ii) TROSY-type [$^{13}$C, $^1$H]-correlation experiments with the $^{13}$C–$^1$H moieties of the aromatic rings of Tyr, Phe and Trp yield comparable results to those for $^{15}$N–$^1$H moieties (unpublished results). (iii) 2D NOESY experiments correlating amide protons and aromatic protons can be relayed by TROSY-type heteronuclear correlation experiments. In favorable cases this might result in low resolution structures for several-fold larger proteins than have been accessible so far. (iv) We anticipate that a wide variety of NMR experiments currently employed for resonance assignments and collection of conformational constraints can be optimized for larger molecular sizes by use of the TROSY approach in one or several dimensions.

Figure 1:
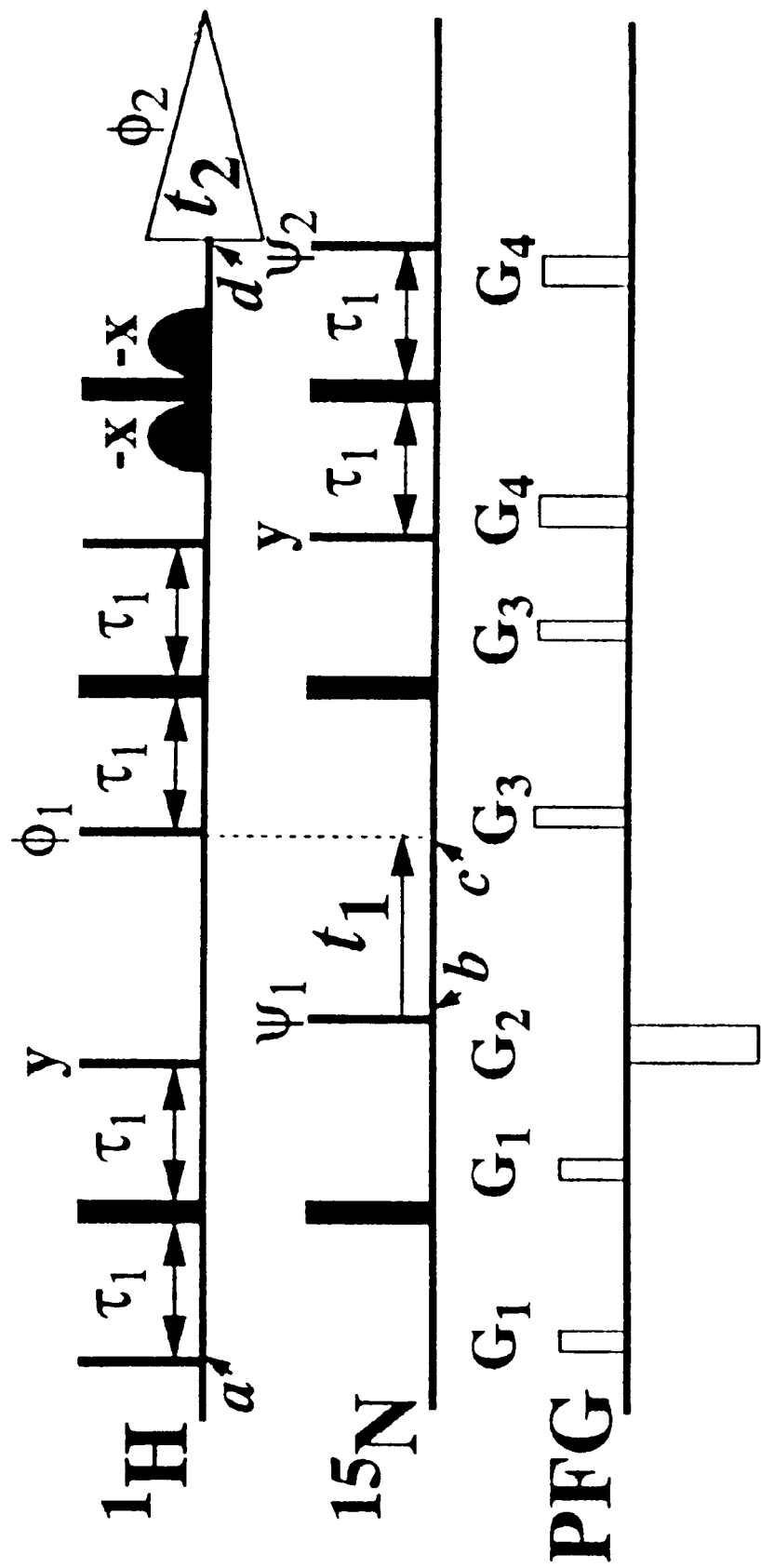
FIG. 1. Experimental scheme for TROSY-type 2D $^1$H, $^{15}$N correlation spectroscopy. In the rows marked $^1$H and $^{15}$N, narrow and wide bars stand for non-selective 90° and 180° rf pulses, respectively. Water suppression is achieved by WATERGATE (34), using the two off-resonance rf pulses indicated by curved shapes. The $^1$H and $^{15}$N carrier frequencies are placed at 9 and 127 ppm, respectively. The delay $\tau_1$ corresponds to $1/(4^1J(^1H, ^{15}N))=2.7$ ms. Phases used are $\psi_1=\{y, -y, -x, x, y, -y, -x, x\}$; $\psi_2=\{4(x), 4(-x)\}$; $\phi_1=\{4(y), 4(-y)\}$; $\phi_2$ (receiver)=$\{x, -x, -y, y, x, -x, y, -y\}$; x on all other pulses. The row marked PFG indicates the applied magnetic field gradients along the z-axis: $G_1$, amplitude=30 G/cm, duration=0.4 ms; $G_2$, -60 G/cm, 1 ms; $G_3$, 50 G/cm, 0.4 ms; $G_4$, 48 G/cm, 0.6 ms. Two FIDs are recorded per $t_1$ delay, with $\psi_1$ incremented by 90° in-between, and stored as the real and imaginary parts of the interferogram in $t_1$. The Fourier transformation results in a 2D $^1$H, $^{15}$N correlation spectrum which contains only the component of the four-line $^{15}$N–$^1$H multiplet that has the slowest $T_2$ relaxation rates for both nuclei.

The coherence transfer during the pulse sequence of FIG. 1 was evaluated using the product operator formalism (Sørensen, O. W., Eich, G. W., Levitt, M. H., Bodenhausen, G. & Ernst, R. R. (1983) *Prog. NMR Spectrosc.* 16, 163–192) as implemented in the program POMA (Güntert, P., Schaefer, N., Otting, G. & Wüthrich, K. (1993) *J. Magn. Reson.* 101, 103–105), and the resulting phases of the rf-pulses and the receiver were transferred into the experimental pulse program according to (Levitt, M. H. (1997) *J. Magn. Reson.* 126, 164–182). The transverse proton magnetization after the first 90° pulse on protons (a in FIG. 1) is then given by Eq. [8]:

$$\sigma(a) = -I_y. \qquad [8]$$

During the delay $2\tau_1$ the scalar coupling $^1J(^1H, ^{15}N)$ evolves, so that the first 90° ($^{15}$N) pulse generates two-spin coherence. With $\tau_1 = 1/(4 ^1J(^1H, ^{15}N))$ we have at time b for the first step of the phase cycle (FIG. 1):

$$\sigma_1(b) = 2I_zS_x = I_zS^- + I_zS^+ (\psi_1 = y) \qquad [9]$$

The evolution of these terms during $t_1$, including relaxation, was evaluated using the single-transition basis operators $S_{12}^\pm$ and $S_{34}^\pm$: \hfill [10]

$$S_{12}^\pm = \frac{1}{2}S^\pm + I_Z S^\pm$$

$$S_{34}^\pm = \frac{1}{2}S^\pm - I_Z S^\pm \qquad [11]$$

The time evolution of the expectation values of these operators can be obtained by integration of Eq. [1] with initial conditions derived from Eq. [9] and the assumption that $1/T_{1I} \ll ^1J(^1H, ^{15}N)$, which results in the following density matrix at time c:

$$\sigma_1(c) = \frac{1}{2}S^-(\exp[i\omega_S^{12}t_1 - R_{12}t_1] - \exp[i\omega_S^{34}t_1 - R_{34}t_1]) + \qquad [12]$$

$$I_Z S^-(\exp[i\omega_S^{12}t_1 - R_{12}t_1] + \exp[i\omega_S^{34}t_1 - R_{34}t_1]) +$$

$$\frac{1}{2}S^+(\exp[-i\omega_S^{12}t_1 - R_{12}t_1] - \exp[-i\omega_S^{34}t_1 - R_{34}t_1]) +$$

$$I_Z S^+(\exp[-i\omega_S^{12}t_1 - R_{12}t_1] + \exp[-i\omega_S^{34}t_1 - R_{34}t_1])$$

The relaxation factors $R_{ij}$ are related to the individual relaxation rates of the multiplet components by Eqs. [13] and [14]:

$$R_{jk} = R_{jkjk} + 1/T_{2S} + 1/(2T_{1I}) \text{ (jk=12, 34)} \qquad [13]$$

$$R_{jk} = R_{jkjk} + 1/T_{2I} + 1/(2T_{1S}) \text{ (jk=13, 24)} \qquad [14]$$

The subsequent polarization transfer step (time period c to d in FIG. 1) links the evolution period $t_1$ with the acquisition period $t_2$. The density matrix at time point c is represented by Eq. [15], where only those $\Gamma$ and $\Gamma S_z$ coherences are retained that result in detectable signals during data acquisition:

$$\sigma_1(d) = \frac{1}{2}\Gamma(i\cos[\omega_S^{12}t_1] - \sin[\omega_S^{12}t_1])\exp[-R_{12}t_1] + \qquad [15]$$

$$\frac{1}{2}\Gamma(i\cos[\omega_S^{34}t_1] + \sin[\omega_S^{34}t_1])\exp[-R_{34}t_1] -$$

$$\Gamma S_Z(i\cos[\omega_S^{12}t_1] - \sin[\omega_S^{12}t_1])\exp[-R_{12}t_1] +$$

$$\Gamma S_Z(i\cos[\omega_S^{34}t_1] + \sin[\omega_S^{34}t_1])\exp[-R_{34}t_1]$$

The other steps in the phase cycle of FIG. 1 can be analysed in an analogous fashion. Accumulation of the 8 transients of the pulse sequence results in the following spectral density matrix for the real part of the interferogram:

$$\sigma_{Re}(d) = -4\Gamma\sin[\omega_S^{12}t_1]\exp[-R_{12}t_1] + \quad [16]$$

$$8\Gamma S_Z\sin[\omega_S^{12}t_1]\exp[-R_{12}t_1]$$

Incrementation of the phase $\psi_1$ by 90° at each discrete value of $t_1$ leads to the corresponding imaginary part:

$$\sigma_{Im}(d) = -4\Gamma\cos[\omega_S^{12}t_1]\exp[-R_{12}t_1] + \quad [17]$$

$$8\Gamma S_Z\cos[\omega_S^{12}t_1]\exp[-R_{12}t_1]$$

The equations [16] and [17] are combined to the hypercomplex interferogram that represents pure phase correlation in the $\omega_1$ dimension.

The treatment of the relaxation of the $^1H^N$ coherences during the acquisition period $t_2$ is similar to the treatment of $^{15}N$ during $t_1$ (see Theory). The signals generated by $\Gamma$ and $\Gamma S_z$ coherences that are received during $t_2$ are described by Eqs. [18] and [19], respectively:

$$\Gamma \to A(\exp[i\omega_I^{13}t_2 - R_{13}t_2] + \exp[i\omega_I^{24}t_2 - R_{24}t_2]) \quad [18]$$

$$2\Gamma S_Z \to A(\exp[i\omega_I^{13}t_2 - R_{13}t_2] - \exp[i\omega_I^{24}t_2 - R_{24}t_2]), \quad [19]$$

where A is a proportionality coefficient. Substitution of Eqs. [18] and [19] into Eqs. [16] and [17] results in the hypercomplex interferogram corresponding to the 1→2 and 2→4 transitions of the $^1H$, $^{15}N$ spin system:

$$\sigma_{1224} = 8A\exp[i\omega_S^{12}t_1 + i\omega_I^{24}t_2]\exp[-(R_{12}t_1 + R_{24}t_2)] \quad [20]$$

Finally, the Fourier transformation of the hypercomplex interferogram represented by Eq. [20] results in the pure absorptive correlation spectrum, with resonance frequencies in $\omega_1$ and $\omega_2$ corresponding to the desired individual component of the $^{15}N$–$^1H$ multiplet.

We claim:

1. A method for obtaining a nuclear magnetic resonance (NMR) correlation spectrum of a heteronuclear spin system, the spin system being subjected to a homogeneous magnetic field $B_0$ and irradiated with a sequence of radio frequency (rf) pulses, the method comprising the steps of:
    a) selecting the spin system to comprise a first spin ½ nuclei I and a second spin ½ nuclei S, said first and said second nuclei being coupled to each other;
    b) cross correlating dipole—dipole coupling and chemical shift anisotropy of said first and said second nuclei; and
    c) mutually cancelling relaxation effects due to dipole—dipole coupling and chemical shift anisotropy, wherein relaxation rates of individual multiplet components of the spin system are changed and line broadening due to the transverse relaxation ($T_2$) reduced.

2. The method of claim 1, further comprising suppressing NMR signals of a solvent.

3. The method of claim 2, wherein NMR signals of water are suppressed.

4. The method of claim 3, wherein a WATERGATE pulse sequence is used comprising two off-resonance rf pulses at an end of the sequence just before data acquisition.

5. The method of claim 1, further comprising exclusively recording NMR signals of a multiplet component for which a residual linewidth is dominated by DD interactions with remote hydrogen atoms in a protein.

6. The method of claim 5, wherein said DD interactions are reduced by $^2H$-labelling.

7. The method of claim 1, further comprising obtaining a heteronuclear correlation spectrum for use in a second experiment.

8. The method of claim 7, wherein said second experiment is a NOESY experiment correlating amide protons and aromatic protons.

9. A method for obtaining a nuclear magnetic resonance (NMR) correlation spectrum of a heteronuclear spin system, the spin system being subjected to a homogeneous magnetic field $B_0$ and irradiated with a sequence of radio frequency (rf) pulses, the method comprising the steps of:
    a) irradiating a first non-selective 90° pulse onto first spin ½ nuclei I;
    b) waiting a first delay time $\tau_1$ following step a);
    c) irradiating a first non-selective 180° pulse onto said I nuclei and a second nonselective 180° pulse onto second spin ½ nuclei S;
    d) waiting a second delay time $\tau_1$ following step c);
    e) irradiating a second non-selective 90° pulse $\psi_1$ onto said I nuclei;
    f) irradiating a first phase-cycled 90° pulse $\psi_1$ onto said S nuclei;
    g) waiting an evolution time $t_1$ following step f);
    h) irradiating a second phase-cycled 90° pulse $\phi_1$ onto said I nuclei;
    i) waiting a third delay time $\tau_1$ following step h);
    j) irradiating a third non-selective 180° pulse on said I nuclei and a fourth non-selective 180° pulse on said S nuclei;
    k) waiting a fourth delay time $\tau_1$ following step j);
    l) irradiating a third non-selective 90° pulse onto said I nuclei, and a fourth non-selective 90° pulse onto said S nuclei;
    m) waiting a fifth delay time $\tau_1$ following step l);
    n) irradiating a fifth non-selective 180° pulse on said I nuclei and sixth non-selective 180° pulse on said S nuclei;
    o) waiting a sixth delay time $\tau_1$;
    p) irradiating a third phase-cycled 90° pulse $\psi_2$ onto said S nuclei; and
    q) acquiring data during a time $t_2$.

10. The method of claim 9, further comprising applying at least one of a $G_1$, $G_2$, $G_3$, and $G_4$ magnetic field gradient of different strength during at least one of said first, second, third, fourth, fifth and sixth delay times $\tau_1$ and applying said $G_2$ magnetic field gradient directly before irradiating said first phase-cycled pulse $\psi_1$.

11. The method of claim 9, wherein no refocussing actions are performed with respect to said I and said S nuclei during said evolution time interval $t_1$ and during said acquisition time period $t_2$, whereby averaging of different relaxation rates and elimination of DD and CSA interference is avoided during these periods.

12. The method of claim 11, wherein no 180° refocussing rf pulse is irradiated during INEPT transfer and during all evolution periods.

13. The method of claim 9, further comprising suppressing NMR signals of a solvent.

14. The method of claim 13, wherein NMR signals of water are suppressed.

15. The method of claim 14, wherein a WATERGATE pulse sequence is used comprising two off-resonance rf pulses at an end of the sequence just before data acquisition.

16. The method of claim 9, further comprising exclusively recording NMR signals of a multiplet component for which a residual linewidth is dominated by DD interactions with remote hydrogen atoms in a protein.

17. The method of claim 16, wherein said DD interactions are reduced by $^2$H-labelling.

18. The method of claim 9, further comprising obtaining a heteronuclear correlation spectrum for use in a second experiment.

19. The method of claim 18, wherein said second experiment is a NOESY experiment correlating amide protons and aromatic protons.

* * * * *